(12) United States Patent
Johnston et al.

(10) Patent No.: US 11,806,055 B2
(45) Date of Patent: Nov. 7, 2023

(54) CUSTOMIZED BONE DISTRACTION METHOD, DEVICE AND SYSTEM

(71) Applicant: KLS Martin, Inc., Jacksonville, FL (US)

(72) Inventors: Thomas S. Johnston, Jacksonville, FL (US); Michael Mantia, Jacksonville, FL (US); Christopher Derderian, Dallas, TX (US)

( * ) Notice: Subject to any disclaimer, the term of this patent is extended or adjusted under 35 U.S.C. 154(b) by 161 days.

(21) Appl. No.: 17/027,347

(22) Filed: Sep. 21, 2020

(65) Prior Publication Data

US 2021/0085377 A1 Mar. 25, 2021

Related U.S. Application Data

(60) Provisional application No. 62/902,758, filed on Sep. 19, 2019.

(51) Int. Cl.
| | |
|---|---|
| *A61B 17/80* | (2006.01) |
| *A61B 17/15* | (2006.01) |
| *A61B 34/10* | (2016.01) |
| *A61B 17/56* | (2006.01) |
| *A61B 17/68* | (2006.01) |

(52) U.S. Cl.
CPC ........ *A61B 17/8019* (2013.01); *A61B 17/151* (2013.01); *A61B 34/10* (2016.02); *A61B 17/8071* (2013.01); *A61B 2017/564* (2013.01); *A61B 2017/681* (2013.01); *A61B 2034/105* (2016.02); *A61B 2034/108* (2016.02)

(58) Field of Classification Search
CPC .............. A61B 17/025; A61B 17/8085; A61B 17/8061; A61B 2017/0256; A61B 2017/681

See application file for complete search history.

(56) References Cited

U.S. PATENT DOCUMENTS

| | | | | |
|---|---|---|---|---|
| 2009/0254126 | A1* | 10/2009 | Orbay | A61B 17/8004 606/301 |
| 2012/0277749 | A1* | 11/2012 | Mootien | A61B 17/8875 606/70 |
| 2014/0163576 | A1* | 6/2014 | Knoepfle | A61B 17/663 606/105 |

\* cited by examiner

*Primary Examiner* — Sameh R Boles
(74) *Attorney, Agent, or Firm* — Thomas C. Saitta

(57) ABSTRACT

A bone distractor device and method of bone distraction in osteogenesis, the bone distractor having releasable bone plates, created using computer-aided design to conform to the surface of a bone, attached to a distraction mechanism, wherein the distractor device is affixed to the bone, the distraction mechanism is removed from the bone plates, the osteotomy is performed using a guide edge provided on at least one of the bone plates, and the distraction mechanism is re-attached to the bone plates such that distraction can be initiated.

5 Claims, 3 Drawing Sheets

CUSTOMIZED BONE DISTRACTION METHOD, DEVICE AND SYSTEM

BACKGROUND OF THE INVENTION

This application relates generally to bone distraction methods, devices and systems for osteogenesis, wherein an osteotomy is performed on a bone to separate a first portion of the bone from a second portion, a distractor device is affixed across the osteotomy, the distractor device comprising a distraction mechanism and a pair of bone plates or implants structured for affixation to the bone segments, one plate being affixed to a first bone segment and the other plate being affixed to a second bone segment, and the distractor device is incrementally actuated to separate the bone plates during bone regeneration in order to elongate the bone.

This application further relates to customized, computer-aided bone distraction methods and systems, wherein patient-specific customized bone plates or footplates matching the contours of the patient's anatomy are provided, the bone plates having been designed using virtual planning based on digitized data derived from the patient's anatomy, such as for example CT scan data. In a typical method, a virtual three-dimensional model of the bone is created, virtual bone plate templates conforming to the surface topography of the bone are created based on the virtual three-dimensional model, and then actual bone plates are produced based on the virtual bone plate templates. In this manner the customized bone plates conform to the surface topography or configuration of the patient's bone to provide an optimized fit onto the bone segments, including the locations of the mounting apertures so as to receive bone screws in the optimum locations for secure attachment and reduced damage to nerves or weak bone portions. Examples of computer-aided implant formation methodology are shown in U.S. Pat. Nos. 8,781,557, 9,066,733, and 9,339,279, the disclosures of which are incorporated herein by reference.

The use of distractor devices to modify or reconstruct bones through osteogenesis is well known in the art. Such systems and methods are utilized in connection with mandibles, maxillae, midface, palates, craniums, thoracic bones and others. In a basic embodiment, the surgeon takes standardized, pre-manufactured bone plates (e.g., rectangular plates with an evenly spaced array of holes to receive bone screws) and contours the bone plates to the patient anatomy by hand. The surgeon then cuts then off the portion of the plate that is not needed and hopes that they are able to position the device such that it is in the proper vector. The use of computer-aided implant design in the non-distractor, i.e., fixed, systems and methods is also well known in the art. In this advanced embodiment, the surgeon, working from patient CT or similar computer-aided data showing patient anatomy, either alone or in conjunction with computer skilled technicians, determines the desired reconfiguration or movement of the bone, the optimum vector for distraction, which distraction device is preferred, where the osteotomy should be performed, and where the screw holes should be situated. A planned case report is prepared and an anatomical model is provided to the surgeon. The surgeon uses the plan and the model to contour standard bone plates, already attached to the distraction mechanism, and cuts off unnecessary portions of the plates. The surgeon then uses a provided cutting or marking guide to mark a few screw holes and the desired location and orientation of the osteotomy directly on the bone. If a cutting guide is provided, the guide is temporarily affixed to the bone and is used to cut the osteotomy. The cutting guide is then removed and the distraction device is mounted to the bone segments by affixing the bone plates, the distraction device being oriented and located as close to the optimum location and orientation as shown in the plan as they can get, which is dependent on the surgeon's ability to properly contour the bone plate and find the marked screw holes.

These and other known devices, systems and methods suffer from certain problems. For example, in the creation of typical customized distractor bone plates, the optimal distraction vector is not taken into consideration, such that the final configuration of the bone after osteotomy, elongation and then regeneration may not be optimal. Another problem is that plates are affixed after the osteotomy has been performed, making it more difficult to properly position and attach each bone plate on its bone segment, especially if one of the bone segments is unanchored, such as will occur for example with the anterior segment of a mandible if an osteotomy has been performed on both sides. Still another problem is that the osteotomy is performed freeform or with a separate cutting guide member.

It is an object of this invention to address these problems in various embodiments of the device, system and method. It is an object of this invention to provide an improved bone distraction device, method and system, wherein patient specific customized bone plates matching the patient's anatomy are provided, the bone plates having been designed using computer-aided virtual planning based on the patient's anatomy, whereby in addition to providing customized contoured bone plates relative to the anatomy, the location and orientation of the bone plates relative to the distraction mechanism is based on the desired distraction vector as determined by the surgeon. In this manner, when the bone plates are affixed to the bone segments using mechanical fasteners, the distraction mechanism will be properly oriented on the desired distraction vector once it is attached to the bone plates. It is a further object to provide a device, system and method wherein in certain embodiments the bone plates are created independent of the distraction mechanism, such that the bone plates are mechanically fastened, in interlocking manner or with mechanical fasteners, to the distraction mechanism, in a manner allowing for attachment, detachment and re-attachment. It is a further object to provide a device, system and method wherein in certain embodiments a set of bone plates is attachable to various types of distractor mechanisms. It is a further object to provide a device, system and method wherein in certain embodiments at least one of the bone plates includes a cutting guide structure, such that the distraction device with attached bone plates can be affixed to the bone prior to creation of the osteotomy, the distraction mechanism removed from the bone plates to expose the cutting guide structure, the osteotomy performed with the bone plates affixed to the bone, and the distraction mechanism then re-attached to the bone plates.

SUMMARY OF THE INVENTION

The invention in various embodiments is a device, system and method of distraction osteogenesis wherein patient-specific, customized bone or foot plates matching the surface contours of the patient's anatomy are provided, the bone plates having been designed using computer-aided virtual planning based on the patient's anatomy, whereby in addition to providing customized, contoured bone plates relative to the anatomy, the location and orientation of the bone plates relative to the distraction mechanism is based on the desired distraction vector as previously determined by the surgeon.

A computer-aided, virtual three dimensional model of the bone to be distracted is produced based on actual patient data showing patient anatomy. The optimal operational parameters are then determined, such as the desired reconfiguration or movement of the bone, the optimum vector for distraction, which distraction device is preferred, the location of the osteotomy to be performed, and the best locations for the screw holes. A preferred distraction mechanism or body is chosen and the desired bone plate shape and thickness is determined. Screw hole locations designed to find the best bone portions for secure attachment and to avoid damage to tissues, nerves, tooth roots, etc. are determined. From this input, virtual bone plate templates are produced having inner surfaces matching the surface contours, topography or configuration of the patient at the chosen affixation locations. This design information is then used to produce actual bone plates based on the virtual bone plates for connection to a distraction mechanism and implantation on the patient's bone.

In a preferred embodiment, the surgeon assembles the distractor device by attaching the modular bone plates onto the distraction mechanism. The fully assembled distractor device is then positioned and the bone plates are affixed to the bone with mechanical fasteners such as bone screws. Because the bone plates are contoured to the specific patient anatomy at chosen locations, the bone plates will only fit in the proper locations. The distraction mechanism is removed from the bone plates. The surgeon then cuts between the bone plates using a guide edge on at least one of the bone plates as a cutting guide. The bone plates may be configured such that a cutting gap is present between and defined by the two bone plates. Furthermore, at least one of the bone plates may be provided with a cutting guide shoulder, such as a raised or thickened edge portion, to help the surgeon make the osteotomy in the desired shape and location. The distraction mechanism is then screwed back on to bone plates. In this manner proper orientation and placement is guaranteed because the bone plates can only be affixed in one location on the bone and the distraction mechanism can only attach to the affixed bone plates in previously determined orientation such that the distractor mechanism is in the proper position and aligned on the proper vector.

In some cases, the surgeon may want a plate or multiple bone plates to remain affixed to the patient permanently on the bone after distraction and regeneration has been accomplished. These bone plates may be designed to be thickened and contoured on the exterior surface to increase strength or to provide a desired base for cosmetic purposes.

In alternative summary, the invention is a bone distractor device comprising: a distractor mechanism, a first bone plate and a second bone plate, wherein the first bone plate and second bone plate are releasably attached to the distractor mechanism and structured for attachment to a bone, and wherein the first bone plate and the second bone plate are configured using computer-aided design to conform to the exterior surface of the bone; wherein at least one of the first bone plate and second bone plate is provided with a guide edge, the guide edge determining the location of an osteotomy and guiding a bone saw through the bone after the distractor device is affixed to the bone and the distractor mechanism is detached from the first and second bone plates. The invention may further comprise such device wherein the at least one of the first bone plate and second bone plate having a guide edge further comprises a guide shoulder; wherein the guide edge is provided on both the first bone plate and the second bone plate; may further comprise a first connector assembly attaching the first bone plate to the distractor mechanism and a second connector assembly attaching the second bone plate to the distractor mechanism; the first connector assembly comprising a plate connector extension disposed on the first bone plate, a plate connector member disposed on the plate connector extension, a body connector member disposed on the distractor mechanism, and a connection fastener received in the body connector member which mates with the body connector member; the second connector assembly comprising a plate connector extension disposed on the second bone plate, a plate connector member disposed on the plate connector extension, a body connector member disposed on the distractor mechanism, and a connection fastener received in the body connector member which mates with the body connector member; and/or wherein the exterior surfaces of the first bone plate and the second bone plate are configured to present a cosmetically appealing support surface for overlying tissue.

Alternatively, the invention is a bone distraction method comprising the steps of: creating a virtual three-dimensional model of a bone to be distracted using computer-aided design; determining desired affixation locations on the virtual three-dimensional model for a first bone plate and a second bone plate and determining a desired distraction vector; creating a virtual three-dimensional template of a first bone plate and a virtual three-dimensional template of a second bone plate such that the inner surface of the virtual three-dimensional first bone plate template conforms to the surface topography of the bone at the desired attachment location for the virtual three-dimensional first bone plate template on the virtual three-dimensional model and the inner surface of the virtual three-dimensional second bone plate template conforms to the surface topography of the bone at the desired attachment location virtual three-dimensional second bone plate template on the virtual three-dimensional model; determining the desired osteotomy location on the bone, and creating a virtual guide edge defining the desired osteotomy location on at least one of the virtual three-dimensional first bone plate template and second bone plate template; creating a first bone plate based on the virtual three-dimensional first bone plate template and a second bone plate based on the virtual three-dimensional second bone plate template, the inner surfaces of each bone plate conforming to the exterior surface of the bone at the affixation location and the guide edge defining the osteotomy location on the bone; providing a distraction mechanism, wherein the first bone plate and the second bone plate are releasably attachable to the distraction mechanism to create a distractor device such that the distraction mechanism is oriented in the desired distraction vector when the distractor device is affixed to the bone; attaching the first bone plate the second bone plate to the distraction mechanism; affixing the first bone plate and the second bone plate to the bone; detaching the distraction mechanism from the first and second bone plates; performing an osteotomy on the bone using the guide edge to create a first bone segment and a second bone segment wherein the first bone plate is affixed to the first bone section and the second bone plate is affixed to the second bone segment; and re-attaching the bone distractor to the first and second bone plates and incrementally distracting the bone segments during osteogenesis. Further, such method wherein the step of creating a virtual guide edge comprises creating a virtual guide edge on both the virtual three-dimensional first bone plate template and on the virtual three-dimensional second bone plate template.

DETAILED DESCRIPTION OF THE INVENTION

Figure 1:
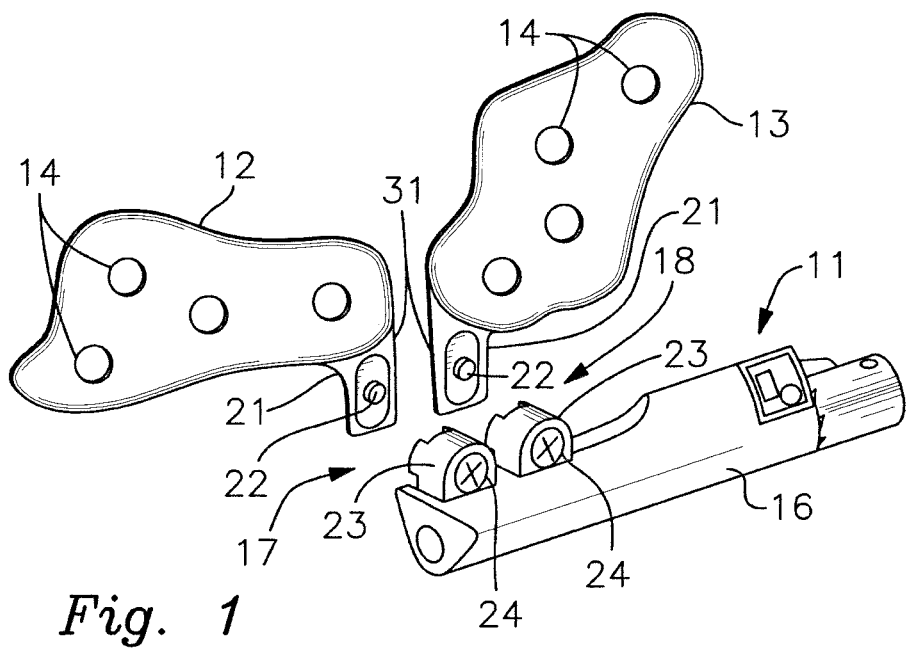
FIG. 1 illustrates an embodiment of a disassembled distractor device, showing a guide edge disposed on one of the bone plates.

With reference to the drawings, which are provided for illustrative and descriptive purposes of disclosure and are not intended to be limiting, the method, device and system of the invention is now described. The invention in various embodiments is a device, system and method of distraction osteogenesis wherein patient-specific, customized bone or foot plates 12/13 matching the surface contours of the patient's bone are provided using known computer-aided design and manufacturing technology, whereby in addition to providing customized, contoured bone plates relative to the bone structure, the location and orientation of the bone plates 12/13 relative to the distraction mechanism 11 is based on the desired distraction vector as previously determined by the surgeon.

A computer-aided, virtual three dimensional model of the bone 90 to be distracted is produced based on actual patient data showing patient anatomy. The optimal operational parameters are then determined, such as the desired reconfiguration or movement of the bone segment or segments 91/92, the optimum vector for distraction, which distractor device 10 is preferred, the location of the osteotomy 93 to be performed, and the best locations for the plate apertures or screw holes 14. A preferred distraction mechanism or body 16 is chosen and the desired bone plate 12/13 shape and thickness is determined. Screw hole 14 locations designed to find the best areas of the bone 90 for secure attachment and to avoid damage to tissues, nerves, tooth roots, etc. are determined. From this input, virtual bone plate templates are produced having inner surfaces matching the surface topography or configuration of the patient's bone 90 at the chosen locations.

In addition to the overall configuration and shape of the bone plates 12/13, a virtual guide edge is determined for at least one of the virtual templates using the computer-aided, virtual three-dimensional model, the virtual guide edge being an indicator for the desired location of the osteotomy 93 and providing a physical structure to at least partially control the movement of the cutting saw during creation of the osteotomy 93. The virtual guide edge may be linear or non-linear as required. All of the design information is then used to produce actual first and second bone plates 12/13 based on the virtual bone plate templates for connection to a distraction mechanism 11 and implantation on the patient's bone 90. Both the first and second bone plates will have inner surfaces corresponding and conforming to the exterior surface of the bone 90 at the affixation location for each. At least one of the first and second bone plates 12/13 is; provided with a cutting guide 31.

In a preferred embodiment, the surgeon assembles the distractor device 10 by attaching the modular first and second bone plates 12/13 onto the distraction mechanism 11 in readily detachable manner. For example, a first connector assembly 17 comprising a plate connector member 22, such as a threaded rod, mounted onto a plate connector extension 21, such as an arm, foot or flange, is structured to releasably mate with a body connection fastener 24, such as an internally threaded screw, retained within a body connector member 23 affixed to the distraction mechanism 11, such that the first bone plate 12 is connected to the distraction mechanism 11 in a manner that allows the distraction member 11 to be detached from and then re-attached to the first body plate 12 after the first body plate 12 has been affixed to the bone 90 using bone screws 15 disposed in screw-receiving apertures 14. In like manner, a second connector assembly 18 comprising a plate connector member 22, such as a threaded rod, mounted onto a plate connector extension 21, such as an arm, foot or flange, is structured to releasably mate with a body connection fastener 24, such as an internally threaded screw, retained within a body connector member 23 affixed to the distraction mechanism 11, such that the second bone plate 13 is connected to the distraction mechanism 11 in a manner that allows the distraction member 11 to be detached from and then re-attached to the second body plate 13 after the second body plate 13 has been affixed to the bone 90 using bone screws 15 disposed in screw-receiving apertures 14. Alternative embodiments for the first and second connector assemblies 17/18 utilizing different connection fasteners or mechanical interlocking structures may be used, provided the bone plates 12/17 are detachable and re-attachable after the bone plates 12/13 have been affixed to the bone 90.

The fully assembled distractor device 10 is positioned on the patient's bone. Because the inner surfaces of the bone plates 12/13 are contoured to conform to the exterior surface of the patient's bone 90, the bone plates 12/13 only seat properly in the desired locations. The bone plates 12/13 are then affixed to the bone 90 with bone screws 15 such as bone screws. The location and orientation of the distractor device 10 now correlates to the desired location and distraction vector as previous determined during the computer-aided design steps.

Figure 2:
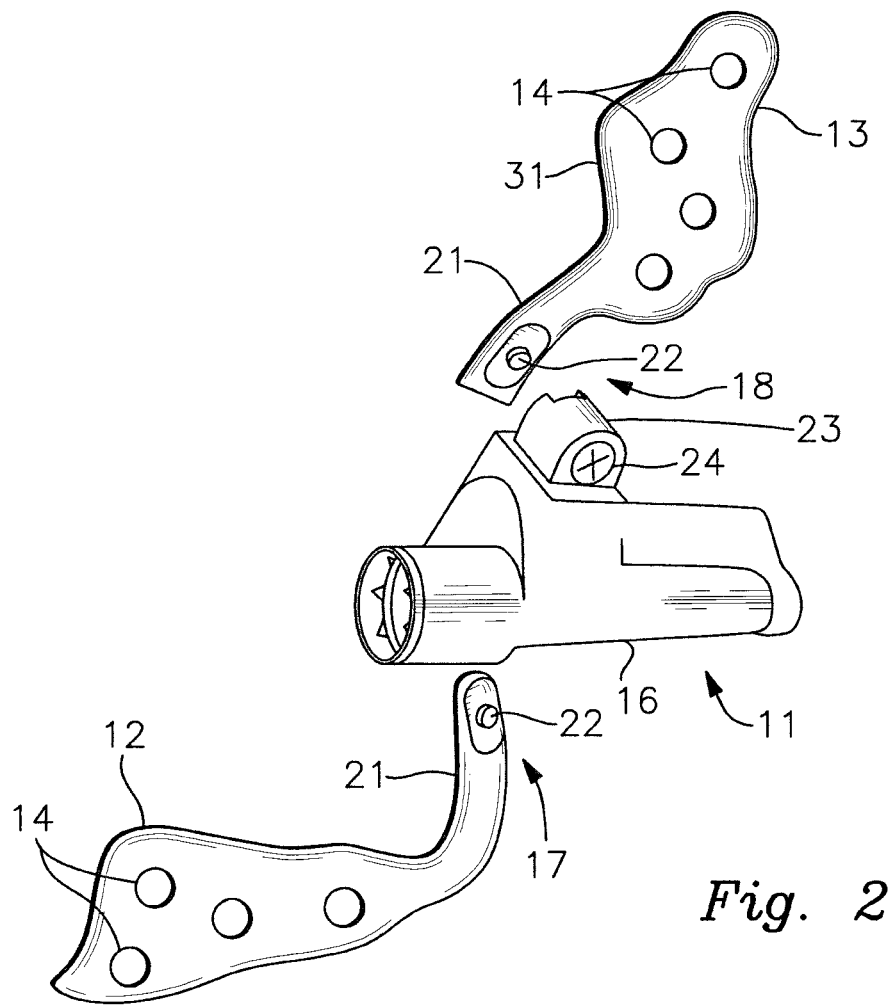
FIG. 2 illustrates an alternative embodiment of a disassembled distractor device, showing a single guide edge on one of the bone plates.
Figure 3:
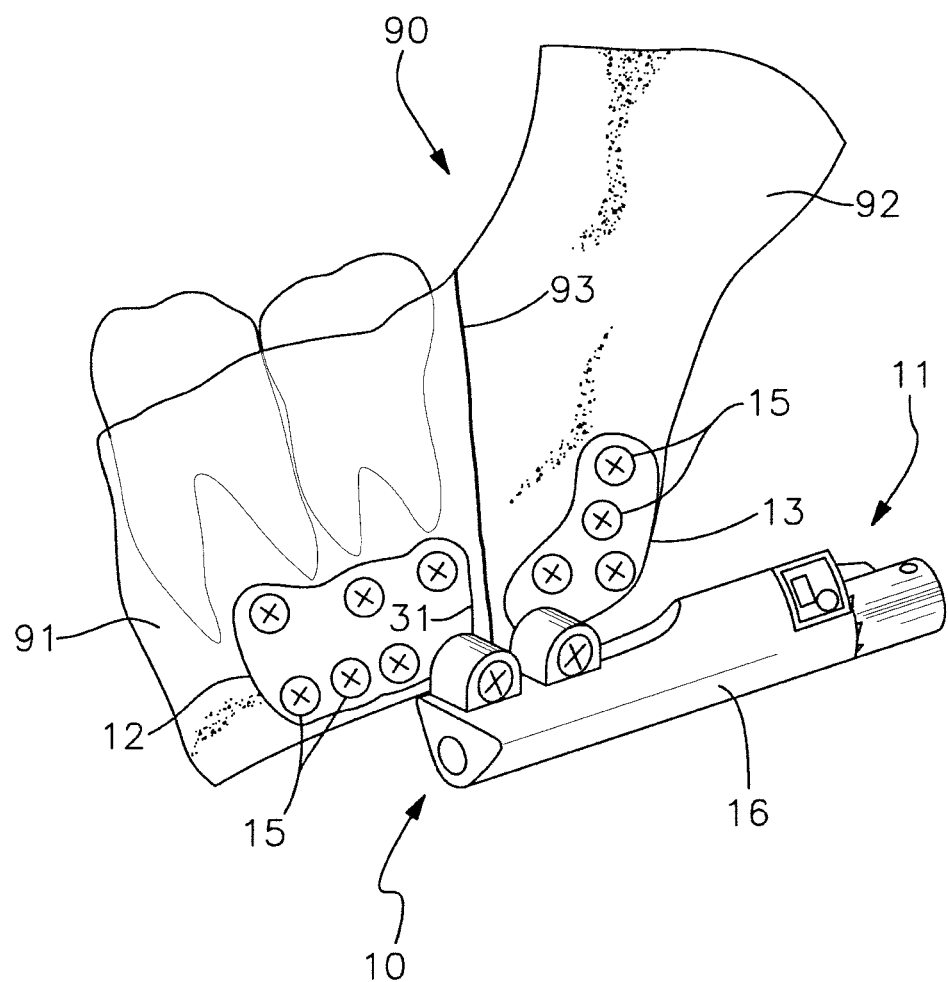
FIG. 3 illustrates an alternative embodiment of a distractor device, the distraction mechanism having been reattached to the bone plates after the osteotomy has been performed.
Figure 4:
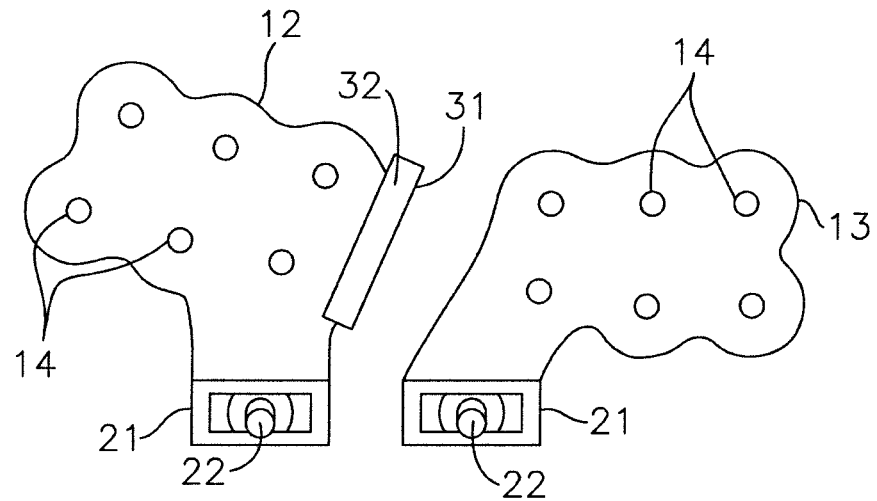
FIG. 4 illustrates an alternative embodiment for the bone plates, showing a guide shoulder and guide edge disposed on one of the bone plates.
Figure 5:
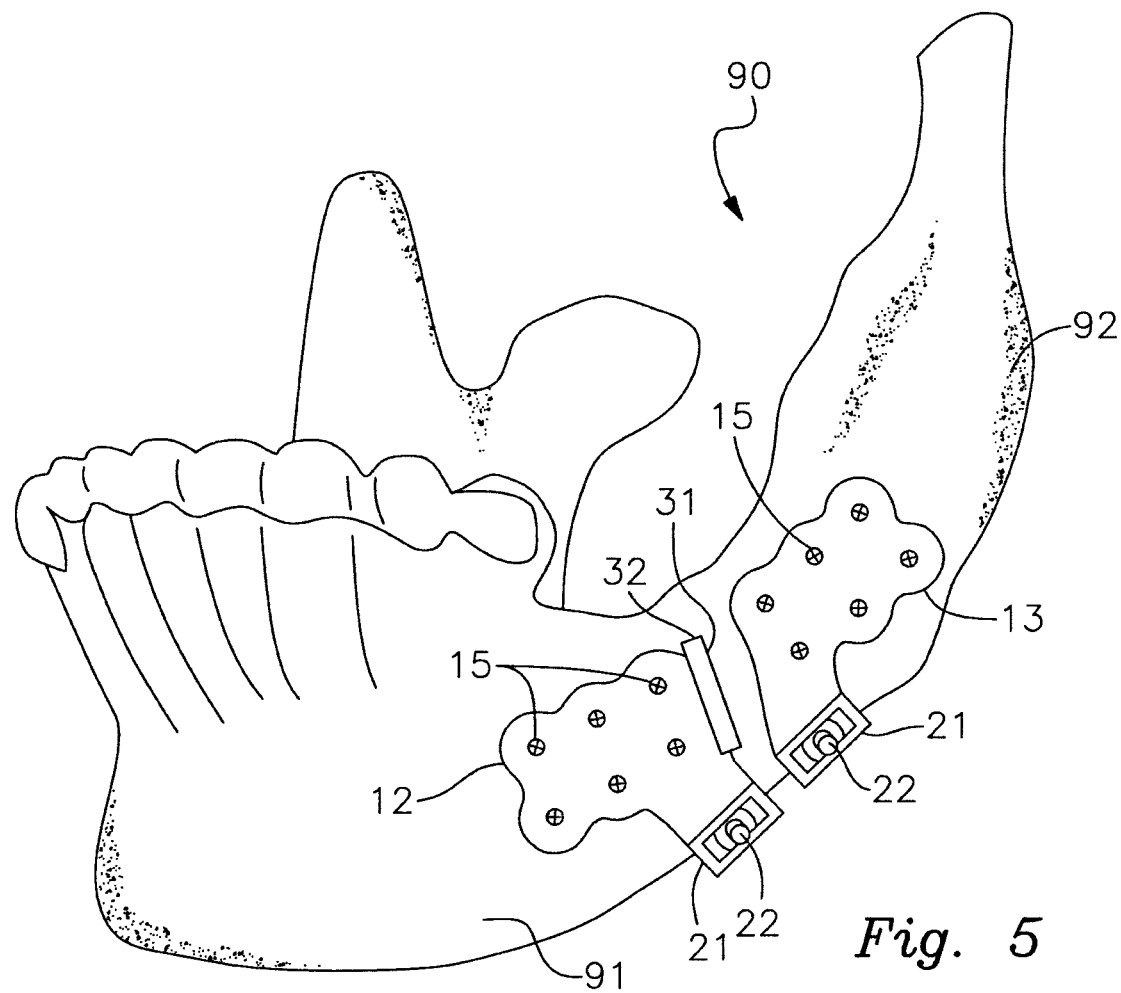
FIG. 5 illustrates the bone plates of FIG. 4 affixed to the bone after the distraction mechanism has been removed and prior to performance of the osteotomy.

The distraction mechanism 15 is then removed from the bone plates 12/13, as shown in FIG. 5. This exposes the guide edge 31, such that the surgeon knows the precise proper location for the osteotomy as previously determined during the computer-aided design stage. The guide edge 31 may be disposed on the first bone plate only, as shown in FIG. 3, on the second bone plate 13, as shown in FIG. 2, or on both bone plates 12/13, as shown in FIG. 1, which creates a defined cutting gap. In a preferred embodiment, as shown in FIGS. 4 and 5, at least one of the bone plates 12/13 is provided with a guide shoulder 32, a raised edge portion at the guide edge 31 which is thicker than the bone plate 12/13 to better guide the cutting saw during the osteotomy.

The surgeon then cuts between the bone plates 12/13, using the guide edge or edges 31 as a cutting guide, to produce a first bone segment 91, to which the first bone plate 12 remains affixed, and a second bone segment 92, to which the second bone plate 13 remains affixed. Once the osteotomy has been performed, as shown in FIG. 3, the distraction mechanism 11 is then re-attached to the bone plates 12/13. In this manner proper orientation and placement of the distractor device 10 is guaranteed because each of the bone plates 12/13 remain properly affixed on the bone segments 91/92 in the pre-chosen location and orientation, and the distraction mechanism can only attach to the affixed bone plates in the previously determined orientation.

With the bone plates 12/13 secured to the distraction mechanism 11, the distractor device 10 may now be utilized in regular manner to slowly reposition and elongated the bone 90 by gradually increasing the distance between the first and second bone segments 91/92 as bone regeneration occurs within the osteotomy gap 93. Once the process is completed, the distraction mechanism 11 and the bone plates 12/13 are removed from the bone 90.

In some cases, it may be beneficial to allow one or both bone plates 12/13 to remain affixed to the patient's bone 90 after distraction and regeneration has been accomplished. These bone plates 12/13 may be designed to be thickened to increase strength, such as where the remaining bone 90 is not as structurally sound as desired, or the bone plates 12/13 may be shaped, contoured and configured on the exterior surface for cosmetic purposes, such that the bone plates 12/13 provide a properly shaped base underlying and supporting the tissue covering the distracted bone 90.

It is understood that substitutions and equivalents for certain elements and steps set forth above may be obvious to those of ordinary skill in the art, and therefore the true scope and definition of the invention is to be as set forth in the following claims.

We claim:

1. A bone distractor device comprising:
a distractor mechanism, body connector members affixed to the distractor mechanism, a first bone plate and a second bone plate, wherein the first bone plate and second bone plate are releasably attached to the body connector members of the distractor mechanism and are structured for attachment to a bone, and wherein the first bone plate and the second bone plate are configured using computer-aided design to conform to the exterior surface of the bone;
wherein at least one of the first bone plate and second bone plate is provided with a guide edge, the guide edge determining the location of an osteotomy and guiding a bone saw through the bone after the distractor device is affixed to the bone and the distractor mechanism is detached from the first and second bone plates;
wherein the at least one of the first bone plate and second bone plate having a guide edge further comprises a guide shoulder, and wherein the guide shoulder comprises a raised portion of the guide edge of greater thickness than the at least one of the first bone plate and second bone plate having a guide edge;
and wherein, with the at least one of the first bone plate and second bone plate provided with a guide edge attached to the body connector members, at least a portion of the guide edge is disposed beyond the body connector members.

2. The bone distractor device of claim 1, wherein the guide edge is provided on both the first bone plate and the second bone plate.

3. The bone distractor device of claim 2, further comprising a first connector assembly attaching the first bone plate to the distractor mechanism and a second connector assembly attaching the second bone plate to the distractor mechanism;
the first connector assembly comprising a plate connector extension disposed on the first bone plate, a plate connector member disposed on the plate connector extension, a body connector member disposed on the distractor mechanism, and a connection fastener received in the body connector member which mates with the body connector member;
the second connector assembly comprising a plate connector extension disposed on the second bone plate, a plate connector member disposed on the plate connector extension, a body connector member disposed on the distractor mechanism, and a connection fastener received in the body connector member which mates with the body connector member.

4. The bone distractor device of claim 1, further comprising a first connector assembly attaching the first bone plate to the distractor mechanism and a second connector assembly attaching the second bone plate to the distractor mechanism;
the first connector assembly comprising a plate connector extension disposed on the first bone plate, a plate connector member disposed on the plate connector extension, a body connector member disposed on the distractor mechanism, and a connection fastener received in the body connector member which mates with the body connector member;
the second connector assembly comprising a plate connector extension disposed on the second bone plate, a plate connector member disposed on the plate connector extension, a body connector member disposed on the distractor mechanism, and a connection fastener received in the body connector member which mates with the body connector member.

5. The bone distractor device of claim 1, wherein the exterior surfaces of the first bone plate and the second bone plate are configured to present a cosmetically appealing support surface for overlying tissue.

* * * * *